US012788303B2

(12) United States Patent
Van der Veen et al.

(10) Patent No.: US 12,788,303 B2
(45) Date of Patent: Nov. 10, 2026

(54) VIRTUAL REALITY BERG BALANCE SCALE

(71) Applicant: Virginia Commonwealth University, Richmond, VA (US)

(72) Inventors: Susanne M. Van der Veen, Richmond, VA (US); James S. Thomas, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 853 days.

(21) Appl. No.: 18/059,115

(22) Filed: Nov. 28, 2022

(65) Prior Publication Data

US 2023/0165512 A1 Jun. 1, 2023

Related U.S. Application Data

(60) Provisional application No. 63/284,584, filed on Nov. 30, 2021.

(51) Int. Cl.
*A61B 5/00* (2006.01)
*G06T 19/00* (2011.01)

(52) U.S. Cl.
CPC .......... *A61B 5/4023* (2013.01); *A61B 5/6801* (2013.01); *A61B 5/6887* (2013.01); *A61B 5/743* (2013.01); *G06T 19/006* (2013.01)

(58) Field of Classification Search
CPC ..... A61B 5/112; A61B 5/1122; A61B 5/1124; A61B 5/4023; A61B 5/6801; A61B 5/6887; A61B 5/743; A61B 5/7475; G06F 1/163; G06F 1/1694; G06F 3/011; G06T 19/006
See application file for complete search history.

(56) References Cited

U.S. PATENT DOCUMENTS

2022/0330854 A1* 10/2022 Jagannathan .......... A61B 5/112
2023/0000396 A1* 1/2023 Coffey .................. A61B 5/1117

* cited by examiner

*Primary Examiner* — Benjamin S Melhus
(74) *Attorney, Agent, or Firm* — Thomas | Horstemeyer, LLP

(57) ABSTRACT

Disclosed are various embodiments of a virtual reality Berg balance scale. A patient can perform a Berg balance test using a virtual reality system. The system can include at least one wearable sensor worn by a patient, and at least one environmental monitor directed towards the patient. A computing device can acquire movement data from the wearable sensor. The computing device can acquire environment data from the environmental monitor. An application on the computing device can then calculate one or more balance scores based at least in part on the movement data and the environment data.

20 Claims, 5 Drawing Sheets

166

VIRTUAL REALITY BERG BALANCE SCALE

CROSS-REFERENCE TO RELATED APPLICATIONS

This application claims priority to, and the benefit of, U.S. Provisional Patent Application No. 63/284,584, entitled "VIRTUAL REALITY BERG BALANCE SCALE" and filed on Nov. 30, 2021, which is incorporated by reference as if set forth herein in its entirety.

BACKGROUND

The Berg Balance Scale (BBS) is a clinical test that allows for clinicians to assess someone's balance and coordination. The BBS can be used for a variety of purposes, such as predicting how long a patient will need to remain admitted to a medical facility or whether the patience will need ambulatory assistance (e.g., a walker) when discharged. However, the BBS has a number of deficiencies. For example, the BBS cannot accurately predict how likely a patient is to fall after being discharged from medical care or how likely the patient is to be readmitted to medical care due to a subsequent fall. Moreover, the BBS requires a trained clinician to assess the patient in person.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
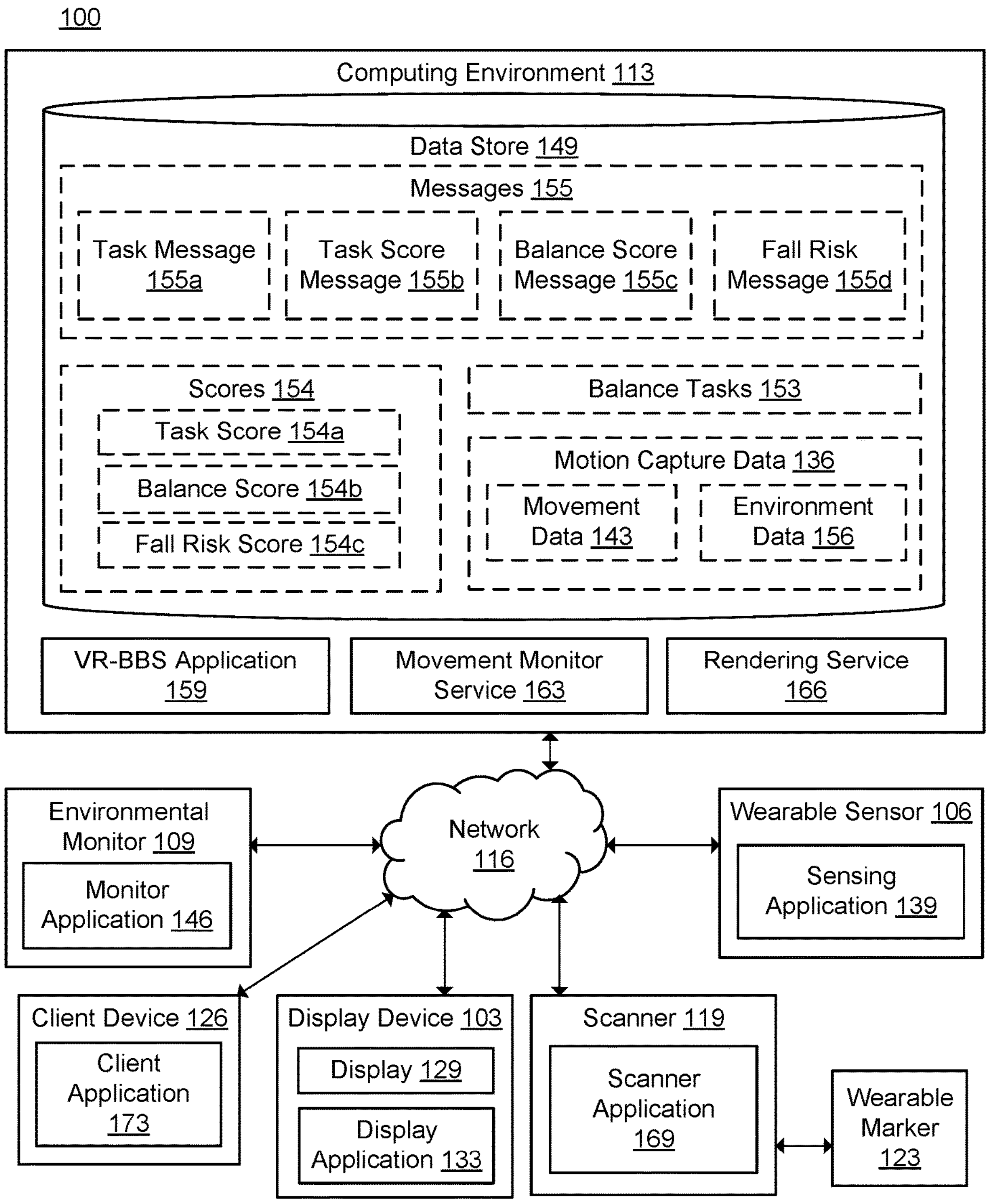
FIG. 1 is a drawing of a network environment according to various embodiments of the present disclosure.

Disclosed are various approaches for using virtual reality or augmented reality equipment to implement a Virtual Berg Balance Scale assessment. The Berg Balance Scale (BBS) consists of fourteen tasks that a patient must complete under a clinician's observation. The clinician must then score each task on a zero to four scale, where zero is scored if the patient is unable to do the task at all, and four if they are perfectly able to complete the task. Therefore, the maximum score a patient can receive under the BBS is fifty-six. A score of less than forty-five is thought to indicate the patient has an increased risk of falling, however, the score is inaccurate to predict fall risk.

Instead of serving as an indicator for fall risk, the BBS can be used for a variety of other purposes, such as predicting how long a patient will need to remain admitted to a medical facility or whether the patient will need ambulatory assistance (e.g., a walker) when discharged. However, the BBS cannot accurately predict a patient's likelihood of falling after being discharged from medical care or the likelihood of readmission to medical care due to a subsequent fall. Moreover, the BBS requires a trained clinician to assess the patient in person.

As such, various embodiments of the present disclosure are directed to systems and methods of utilizing virtual reality or augmented reality equipment to implement a Virtual Berg Balance Scale assessment. To do this, a system can be arranged to administer the BBS and assess a patient's fall risk. The system can instruct the patient to perform a balance task from the BBS, monitor the patient's performance through various sensors, determine the fall risk and/or a balance score for the patient, and report the score to the patient or to a remote clinician.

The system may comprise wearable motion sensors or motion tracking sensors which can be attached to an individual. For example, motion sensors or motion tracking sensors could be attached to an individual's center of mass (e.g., pelvis, torso, etc.), as well as his or her arms, hands, legs, and/or feet. The individual can also wear a virtual reality or augmented reality headset (e.g., an HTC Vive).

As the individual performs various tasks as prompted using the virtual reality headset, the motion sensors or motion tracking sensors can be used to track movement and position data in real time. This real-time data can be used to assess the range of motion, balance, center of mass, etc. of the individual. For example, the individual could perform a Berg Balance Scale assessment in a virtualized environment, and his or her performance of the BBS could be tracked using metrics recorded by the motion sensors or motion tracking sensors.

The collected metrics could then be analyzed using an algorithm. The algorithm could weigh different metrics according to their correlation with balance, coordination, and/or future fall risk. As a result, the algorithm could provide an output that reflects both a user's Berg Balance Scale score and/or a user's likelihood of falling within a predefined future period of time (e.g., within the next 30 days, 60 days, 90 days, etc.). Because the score is calculated algorithmically using the collected data, a trained clinician is not needed to perform the assessment. Likewise, because the assessment is virtualized, it can be performed in any location.

Additionally, a system can be arranged to perform a method of acquiring movement data and environment data from the motion sensors as the patient performs the BBS tasks and using the data to render a real-time virtual environment with a virtual patient which can be viewed on a display device. The patient or a clinician can observe a virtual representation of the patient performing the BBS tasks in the virtual environment portrayed on the display device.

In the following discussion, a general description of the system and its components is provided, followed by a discussion of the operation of the same. Although the following discussion provides illustrative examples of the operation of various components of the present disclosure, the use of the following illustrative examples does not exclude other implementations that are consistent with the principles disclosed by the following illustrative examples.

With reference to FIG. 1, shown is a network environment 100 according to various embodiments. The network environment 100 may include a display device 103, one or more wearable sensors 106, one or more environmental monitors 109, and a computing environment 113, as well as other client or computing devices which can be in data communication with each other via a network 116. In some embodiments, the network environment 100 may also include scanner 119 which can track one or more wearable markers 123 worn by the patient. In some embodiments, the network environment 100 may also include a client device 126.

The network 116 can include wide area networks (WANs), local area networks (LANs), personal area networks (PANs), or a combination thereof. These networks can include wired or wireless components or a combination thereof. Wired networks can include Ethernet networks, cable networks, fiber-optic networks, and telephone networks such as dial-up, digital subscriber line (DSL), and integrated services digital network (ISDN) networks. Wireless networks can include cellular networks, satellite networks, Institute of Electrical and Electronic Engineers (IEEE) 802.11 wireless networks (e.g., WI-FI®), BLUETOOTH® networks, microwave transmission networks, as well as other networks relying on radio broadcasts. The network 116 can also include a combination of two or more networks 116. Examples of networks 116 can include the Internet, intranets, extranets, virtual private networks (VPNs), and similar networks.

The display device 103 can be one or more computing devices that can be coupled to the network 116. The display device 103 may include a processor-based system such as a computer system. Such a computer system can be embodied in the form of a virtual reality headset (e.g., an HTC Vive), a mobile computing device (e.g., personal digital assistants, cellular telephones, smartphones, web pads, tablet computer systems, music players, portable game consoles, electronic book readers, and similar devices), a videogame console, or other devices with like capability. In many embodiments, the display device 103 may be a specialized computing device made specifically for virtual and/or augmented reality. In some embodiments, the display device 103 is a head-mounted display which the patient can wear as a headset. To present the virtual environment, the display device 103 may include one or more displays 129. The display 129 may be a liquid crystal display (LCD), gas plasma-based flat panel display, organic light emitting diode (OLED) display, electrophoretic ink ("E-ink") display, projector, or other types of display screen.

The display device 103 can be configured to execute various applications such as a display application 133 or other applications. The display application 133 can be configured to collect, obtain, and/or receive motion capture data 136 corresponding to the performance of tasks by the patient. Additionally, in some embodiments, the display application 133 can be configured to convert the motion capture data 136 into a virtual environment wherein a virtual patient is shown in a virtual setting performing the same movements as the patient in real time.

One or more wearable sensors 106 can be worn by the patient. In many embodiments, the wearable sensor(s) 106 are attached to a person's center of mass (e.g., pelvis, torso, etc.). Additionally, wearable sensor(s) 106 can be worn on a person's arms, hands, legs, and/or feet. In some cases, the virtual reality headset may include wearable sensor(s) 106 to track the motion of the person's head. In many embodiments, a person can wear more than one wearable sensor 106 over various parts of the body.

The wearable sensor(s) 106 can be one or more computing devices that can be coupled to the network 116. The wearable sensor 106 can include a processor-based system such as a computer system. In many embodiments, the wearable sensor 106 can be a specialized computing device made specifically for collecting movement data of a person. To collect such data, the wearable sensor 106 can include one or more accelerometers, one or more gyroscopes and/or one or more inertial measurement units (IMUs) to measure movement data for a person. The wearable sensor 106 can be configured to execute various applications such as a sensing application 139, or other applications.

The wearable sensor(s) 106 can include one or more accelerometers. Each accelerometer can detect a magnitude and direction of the acceleration of the wearable sensor 106 as it is being moved. The accelerometers can be single-axis or multi-axis accelerometers. A single-axis accelerometer can provide a single value corresponding to a specified axis to the sensing application 139. Using more than one single-axis accelerometers individually collecting data over multiple axes can yield the magnitudes for each axis. Alternatively, the wearable sensor 106 can use one multi-axis accelerometer to yield the same results. In many embodiments, the one or more accelerometers can detect the magnitude of the movement with very great precision. In at least one embodiment, a 3-axis accelerometer is capable of recording the magnitude of movement at 100 Hz.

The wearable sensor(s) 106 can include one or more gyroscopes. Each gyroscope can detect an angular velocity of the wearable sensor 106 as it is being moved and/or rotated. The gyroscopes can be single-axis or multi-axis gyroscopes. A single-axis gyroscope can provide a single value corresponding to a specified axis to the sensing application 139. Using more than one single-axis gyroscope individually collecting data over multiple axes can yield the angular velocity for each axis. Alternatively, the wearable sensor 106 can use one multi-axis gyroscope to yield the same results. In many embodiments, the one or more gyroscopes can detect the angular velocity with very great precision. In at least one embodiment, a 3-axis gyroscope is capable of recording the angular velocity at 100 Hz.

The wearable sensor(s) 106 can include one or more IMUs. Each IMU can detect the specific force, angular rate, linear velocity, and/or orientation of the wearable sensor 106 as it is being moved. The IMUs can include one or more accelerometers, one or more gyroscopes, and one or more magnetometers. In addition to the information that can be provided by the accelerometers and gyroscopes as described in the paragraphs above, the magnetometers can detect the heading of the wearable sensor 106 as it is moved. A plurality of wearable sensors 106 may include a combination of the above disclosed embodiments.

The sensing application 139 can be configured to collect, obtain, and/or receive data corresponding to magnitude of a movement detected by one or more accelerometers. The sensing application 139 can be configured to collect, obtain, and/or receive data corresponding to angular velocity of a movement detected by one or more gyroscopes. Furthermore, the sensing application 139 can be configured to collect, obtain, and/or receive data corresponding to angular velocity of a movement detected by one or more IMUs. The sensing application 139 can combine the collected, obtained, and/or received data from the accelerometers, the gyroscopes, and the IMUs to generate movement data 143 that can be sent to other devices and/or other applications. In at least one embodiment, the sensing application 139 can transmit the movement data 143 over the network 116 to the computing environment 113. In at least another embodiment, the sensing application 139 can transmit the movement data 143 over the network 116 to the display device 103. In at least one embodiment, the sensing application 139 can send the movement data 143 to the display device 103 in real time as the movement data 143 is obtained.

The environmental monitor 109 may be representative of a plurality of environmental monitors 109 that can be coupled to the network 116. The environmental monitor 109 can be one or more computing devices that can be coupled to the network 116. The environmental monitor(s) 109 can include a processor-based system, such as a computer system. In at least one embodiment, the environmental monitor(s) 109 can be a specialized computing devices capable of detecting the patient's environment and tracking the wearable sensor(s) 106 and/or wearable marker(s) 123 as the patient moves within that environment. The environmental monitor 109 may be configured to execute various applications such as a monitor application 146, or other applications. In some embodiments, the environmental monitor 109 is configured to use heat mapping technology to track the patient's movements within the environment. In some embodiments, the environmental monitor 109 can be any device capable of capturing video recordings (e.g., Vicon Vero 2.2 and/or Vantage 5 cameras from Vicon Motion Systems, Ltd, Oxford, UK). For instance, the environmental monitor 109 can be a camcorder (digital or analog), a digital camera capable of capturing video, a mobile computing device capable of capturing video (e.g., personal digital assistants, cellular telephones, smartphones, web pads, tablet computer systems, music players, portable game consoles, electronic book readers, and similar devices), a videogame console, or other like devices capable of capturing video. In at least one embodiment, the environmental monitor 109 can be an analog video camera. The plurality of environmental monitors 109 may comprise a combination of the above listed embodiments.

The environmental monitor(s) 109 can be operated by a person other than the patient. In many embodiments, the environmental monitor(s) 109 can be set up around the patient to collect motion capture data 136 without need for an operator. The environmental monitor 109 can send the motion capture data 136 to the computing environment 113.

The computing environment 113 can include one or more computing devices that include a processor, a memory, and/or a network interface. For example, the computing devices can be configured to perform computations on behalf of other computing devices or applications. As another example, such computing devices can host and/or provide content to other computing devices in response to requests for content.

Moreover, the computing environment 113 can employ a plurality of computing devices that can be arranged in one or more server banks or computer banks or other arrangements. Such computing devices can be located in a single installation or can be distributed among many different geographical locations. For example, the computing environment 113 can include a plurality of computing devices that together can include a hosted computing resource, a grid computing resource, or any other distributed computing arrangement. In some cases, the computing environment 113 can correspond to an elastic computing resource where the allotted capacity of processing, network, storage, or other computing-related resources can vary over time.

In some embodiments, the computing environment 113 can be one or more computing devices that can be coupled to the network 116. The computing environment 113 can include a processor-based system such as a computer system. Such a computer system can be embodied in the form of a personal computer (e.g., a desktop computer, a laptop computer, or similar device), a mobile computing device (e.g., personal digital assistants, cellular telephones, smartphones, web pads, tablet computer systems, music players, portable game consoles, electronic book readers, and similar devices), a videogame console, or other devices with like capability.

In many embodiments, the computing environment 113 can have a data store 149. The data store 149 can be representative of a plurality of data stores 149, which can include relational databases or non-relational databases such as object-oriented databases, hierarchical databases, hash tables or similar key-value data stores, as well as other data storage applications or data structures. Moreover, combinations of these databases, data storage applications, and/or data structures may be used together to provide a single, logical, data store 149. Various data can be stored in the data store 149 that is accessible to the computing environment 113. The data stored in the data store 149 is associated with the operation of the various applications or functional entities described below. This data can include balance tasks 153, scores 154, messages 155, and motion capture data 136 which may comprise movement data 143, environment data 156, and potentially other data.

The motion capture data 136 can represent the movement data 143 obtained by the one or more wearable sensor(s) 106, the one or more environmental monitor(s) 109, and/or by the one or more scanner(s) 119. The movement data 143 can represent any data which depicts the movement of the patient and/or the patient's extremities during the test. The movement data 143 may include the magnitude and direction of the acceleration, the angular velocity, the specific force, angular rate, linear velocity, and/or orientation of the wearable sensor(s) 106 and/or wearable marker(s) 123 as it is being moved, as well as other data that depicts the movement of the patient. The motion capture data 136 can also represent the environment data 156 obtained by the one or more environmental monitor(s) 109 and/or by the scanner(s) 119. The environment data 156 can represent any data which describes the space around the patient and how the patient moves relative to that space. The environment data 156 may include data about the space where the patient will be performing the test, such as whether the space is indoors or outdoors, the dimensions of the space if it is indoors, a center of the space, a relative ground in the space, obstacles that may be in the space which could impact the patient's performance of the test, a heat map of the space and the patient within the space, as well as many other kinds of data. The computing environment 113 can receive the motion capture data from the wearable sensor(s) 106, the environmental monitor(s) 109, and/or the scanner(s) 119 or from other sources. In some embodiments, portions of the environment data 156 can be obtained from a person via a user interface. The motion capture data 136 can be used to assess the patient's range of motion, balance, center of mass, etc.

The computing environment 113 can be configured to execute various applications, services, or other functionality. The components executed on the computing environment 113 can include a Virtual Reality Berg Balance Scale (VR-BBS) application 159, a movement monitor service 163, a rendering service 166 and other applications, services, processes, systems, engines, or functionality not discussed in detail herein. The VR-BBS application 159 can be executed in a computing environment 113 to access network content served up on the network 116, perform a balance analysis, and report the results of the analysis. The VR-BBS application 159 can be executed to at least receive motion capture data 136, calculate one or more scores 154 based at least in part on the motion capture data 136, and send the results to the patient or a clinician.

The scanner 119 may be representative of a plurality of scanners that can be coupled to the network 116. The scanner 119 can be one or more computing devices that can be coupled to the network 116. The scanner 119 can include a processor-based system, such as a computer system. In at least one embodiment, the scanner 119 can be a specialized computing device capable of detecting an environment and the patient's movements within an environment. The scanner 119 may be configured to execute various applications such as a scanner application 169, or other applications. In some embodiments, the scanner 119 can be any device capable of detecting the position of a patient in an environment. In some embodiments, the scanner 119 can use LiDAR technology to scan the environment with a laser and interpret the laser reflections to map the environment and detect movement. In some embodiments, the scanner 119 scans the environment and detects reflections from one or more wearable marker(s) 123 worn by the patient. It at least one embodiment, the scanner 119 is an infrared laser emitter (e.g., HTC Vive Lighthouse, Valve, Washington, USA). The plurality of scanners 119 may be a combination of the above disclosed embodiments.

The client device 126 may be representative of a plurality of client devices 126 that may be coupled to the network 116. The client device 126 can include a processor-based system such as a computer system. Such a computer system can be embodied in the form of a personal computer (e.g., a desktop computer, a laptop computer, or similar device), a mobile computing device (e.g., personal digital assistants, cellular telephones, smartphones, web pads, tablet computer systems, music players, portable game consoles, electronic book readers, and similar devices), media playback devices (e.g., media streaming devices, BluRay® players, digital video disc (DVD) players, set-top boxes, and similar devices), a videogame console, or other devices with like capability. The client device 126 can include one or more displays, such as liquid crystal displays (LCDs), gas plasma-based flat panel displays, organic light emitting diode (OLED) displays, electrophoretic ink ("E-ink") displays, projectors, or other types of display devices. In some instances, the display can be a component of the client device 126 or can be connected to the client device 126 through a wired or wireless connection.

The client device 126 can be configured to execute various applications such as a client application 173, or other applications. The client device 126 can be configured to execute applications beyond the client application 173, such as email applications, social networking applications, word processors, spreadsheets, or other applications.

The client application 173 can be executed to receive real-time motion capture data 136 and/or receive messages 155 and scores 154 through the network 116. The client device 126 may be used by the patient, a clinician, or another individual.

Next, a general description of the operation of the various components of the network environment 100 is provided. Although this general description illustrates the interactions between the components of the network environment 100, other interactions or sequences of interactions are possible in various embodiments of the present disclosure.

To begin, a patient may have a display device 103 and wear one or more wearable sensors 106. The environmental monitor(s) 109 and scanner(s) 119 may detect the patient's start position and the environment surrounding the patient. The movement monitor service 163 can obtain the motion capture data 136 and store the motion capture data 136 in the data store 149. The rendering service 166 may obtain the motion capture data 136 from the data store 149 and render a virtual environment based at least in part on the motion capture data 136. The process of the rendering service 166 is further explained in the discussion of FIG. 2.

The patient may receive an instruction to complete a balance task 153 via a task message 155*a* received on the display device 103. The task message 155*a* may be received, for example, from an application executing on a computing device controlled by a clinician, or as part of an application initiated by the patient. While the patient performs the balance task 153 from the task message 155*a*, the wearable sensor(s) 106, environmental monitor(s) 109, and/or scanner(s) 119 can collect motion capture data 136 from the patient's movements. The movement monitor service 163 can obtain the motion capture data 136 and store the motion capture data 136 in the data store 149. The VR-BBS application 159 can obtain the motion capture data 136 from the data store 149, or from the wearable sensor(s) 106, environmental monitor 109, and scanner(s) 119 directly. The VR-BBS application 159 can analyze the data to interpret join excursions, joint moments, center of mass displacement, and other metrics, and calculate a task score 154*a* based at least in part on the analysis. The task score 154*a* corresponds to the balance task 153 performed by the patient. The patient may receive the next balance task 153 and these steps will be repeated until there is a score 154 for every balance task 153. The VR-BBS application 159 can calculate a balance score 154*b* based at least in part on the individual task scores and can report this balance score to the display device 103 and/or the client device 126. Additionally, the VR-BBS application 159 can calculate a fall risk score 154*c* and report the fall risk score 154*c* to the display device 103 and/or a client device 126. This process involving the VR-BBS application 159 is further explained in the discussion of FIGS. 3 and 4.

Figure 2:
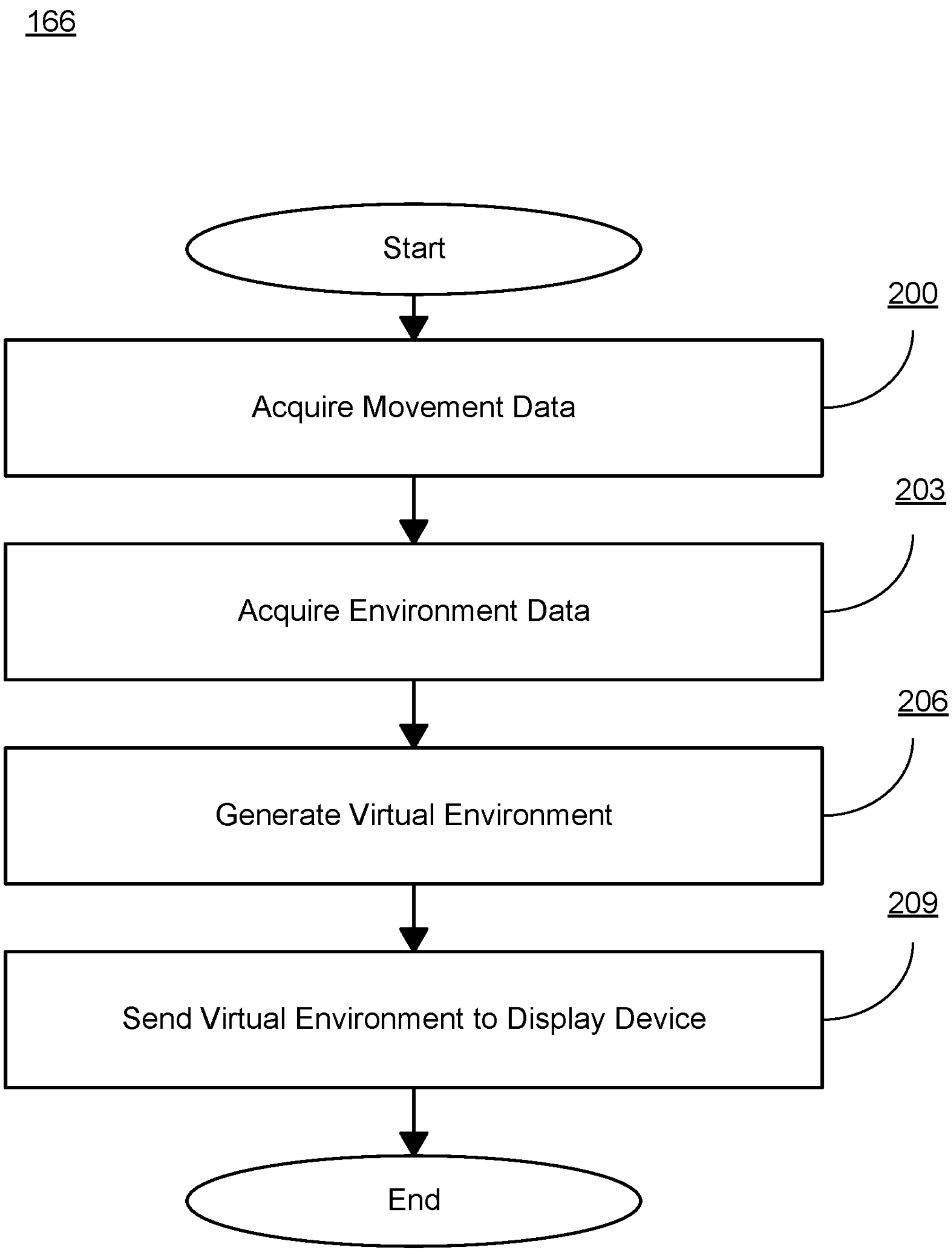
FIG. 2 is a flowchart illustrating one example of functionality implemented as portions of an application executed in the network environment of FIG. 1 according to various embodiments of the present disclosure.

Referring next to FIG. 2, shown is a flowchart that provides one example of the operation of the rendering service 166. The flowchart of FIG. 2 provides merely an example of the many different types of functional arrangements that can be employed to implement the operation of the depicted portion of the rendering service 166. Alternatively, the flowchart of FIG. 2 could be viewed as depicting a method implemented by the computing environment 113.

Beginning with block 200, the rendering service 166 can acquire movement data 143 from the data store 149. Alternatively, the movement data 143 can be acquired by the rendering service 166 from the wearable sensor(s) 106, environmental monitor(s) 109, and/or scanner(s) 119.

At block 203, the rendering service 166 can acquire environment data 156 from the data store 149. Alternatively, the environment data 156 can be acquired by the rendering service 166 from the wearable sensor(s) 106, environmental monitor(s) 109, and/or scanner(s) 119.

At block 206, the rendering service 166 can generate a virtual environment based at least in part on the movement data 143 and the environment data 156. In some embodiments, the rendering service 166 can generate the virtual environment using image recognition to identify objects in the space. In some embodiments, the rendering service 166 can generate the virtual environment based at least in part on one or more user inputs.

At block 209, the rendering service 166 can send the virtual environment to the display device 103. Alternatively, in some embodiments, the rendering service 166 can be executed by the display device 103 and cause the virtual environment to be displayed on the display 129 through the display application 133.

Figure 3:
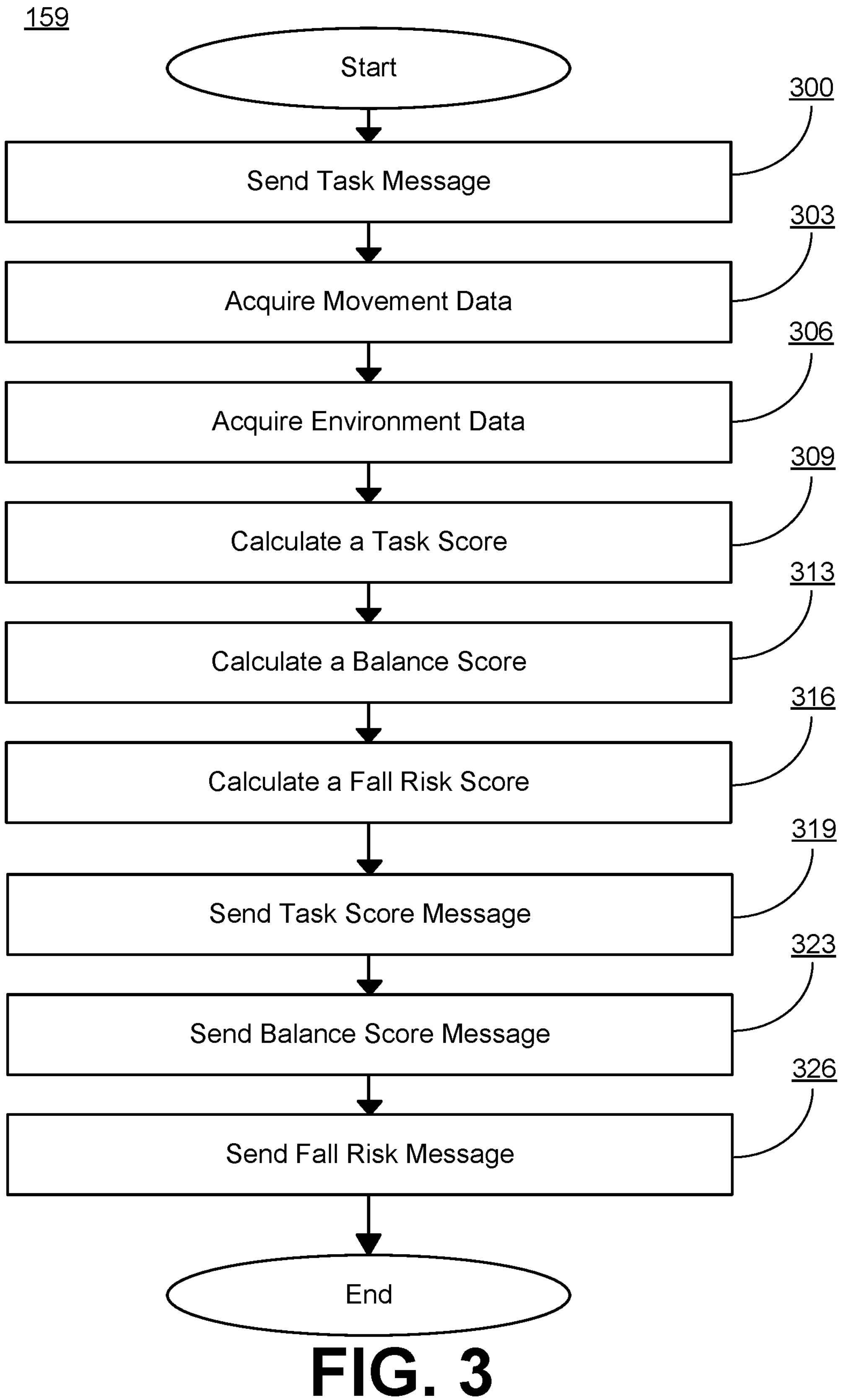
FIG. 3 is a flowchart illustrating one example of functionality implemented as portions of an application executed in the network environment of FIG. 1 according to various embodiments of the present disclosure.

Referring next to FIG. 3, shown is a flowchart that provides one example of the operation of the VR-BBS application 159. The flowchart of FIG. 3 provides merely an example of the many different types of functional arrangements that can be employed to implement the operation of the depicted portion of the VR-BBS application 159. Alternatively, the flowchart of FIG. 3 could be viewed as depicting a method implemented by the computing environment 113.

Beginning with block 300, the VR-BBS application 159 can send a task message 155*a* to a display device 103. The task message 155*a* corresponds to an individual balance task 153 to be performed by the patient. The patient receives the task message 155*a* on the display device 103 and performs the task.

At block 303, the VR-BBS application 159 can acquire movement data 143. In some embodiments, the movement data 143 is obtained from the data store 149. In some embodiments, the movement data 143 is obtained from the wearable sensor(s) 106, environmental monitor(s) 109, and/or scanner(s) 119. The movement data 143 consists of real-time measurements and readings of the patient's movements during the performance of the balance task 153.

At block 306, the VR-BBS application 159 can acquire environment data 156. In some embodiments, the environment data 156 is obtained from the data store 149. In some embodiments, the environment data 156 is obtained from the wearable sensor(s) 106, environmental monitor(s) 109, and/or scanner(s) 119. The environment data 156 consists of real-time measurements and readings of the patient's environment during the performance of the balance task 153.

At block 309, the VR-BBS application 159 can calculate a task score 154*a* based at least in part on the movement data 143 and on the environment data 156. In some embodiments, the calculation is performed using an algorithm based at least in part on the original BBS zero-to-four scoring metrics.

At block 313, the VR-BBS application 159 can calculate a balance score 154*b* based at least in part on the movement data 143, the environment data 156, and the task score 154*a*. In some embodiments, the calculation is performed using an algorithm based at least in part on the original BBS scoring metrics. In some embodiments, the balance score calculation is performed using an algorithm based at least in part on a modified BBS, wherein BBS tasks that would prove hazardous in a virtual reality or augmented reality environment have been removed.

At block 316, the VR-BBS application 159 can calculate a fall risk score 154*c* based at least in part on the movement data 143 and the environment data 156. In some embodiments, the fall risk score 154*c* is calculated based at least in part on a patient's center-of-mass displacement and/or displacement of the pelvis as determined from the movement data 143 and the environment data 156. In some embodiments, the calculation of the fall risk score 154*c* is performed by an algorithm which considers posturography, jerk, amplitude, and range of acceleration as determined from the movement data 143 and the environment data 156. In some embodiments, the calculation of the fall risk score 154*c* is performed by an algorithm which considers the timing of the task and the maxima of acceleration and velocity during the time for the task.

At block 319, the VR-BBS application 159 can send a task score message 155*b* to the display device 103, where the task score message 155*b* corresponds to the task score calculated at block 309. In some embodiments, the VR-BBS application 159 can send the task score message 155*b* to a client device 126.

At block 323, the VR-BBS application 159 can send a balance score message 155*c* to the display device 103, where the balance score message 155*c* corresponds to the balance score calculated at block 313. In some embodiments, the VR-BBS application 159 can send the balance score message 155*c* to a client device 126.

At block 326, the VR-BBS application 159 can send a fall risk message 155*d* to the display device 103, where the fall risk message 155*d* corresponds to the fall risk score 154*c* calculated at block 316. In some embodiments, the VR-BBS application 159 can send the fall risk message 155*d* to a client device 126.

Figure 4:
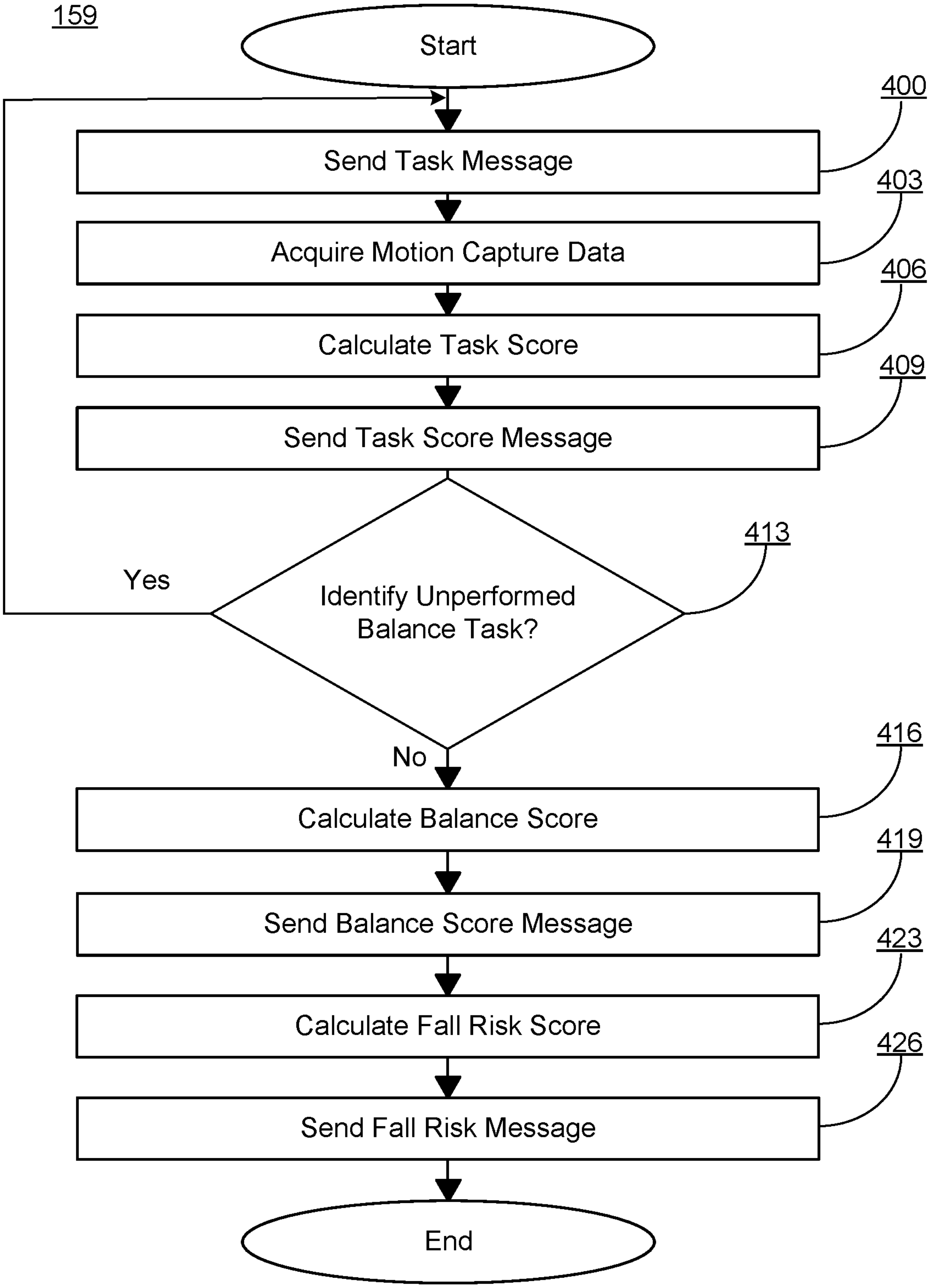
FIG. 4 is a flowchart illustrating one example of functionality implemented as portions of an application executed in the network environment of FIG. 1 according to various embodiments of the present disclosure.

Referring next to FIG. 4, shown is a flowchart that provides one example of the operation of the VR-BBS application 159. The flowchart of FIG. 4 provides merely an example of the many different types of functional arrangements that can be employed to implement the operation of the depicted portion of the VR-BBS application 159. Alternatively, the flowchart of FIG. 4 could be viewed as depicting a method implemented by the computing environment 113.

At block 400, the VR-BBS application 159 can send a task message 155*a* to a display device 103. The task message 155*a* corresponds to an individual balance task 153 to be performed by the patient. The patient can receive the task message 155*a* on the display device 103 and perform the task.

At block 403, the VR-BBS application 159 can acquire motion capture data 136. In some embodiments, the motion capture data 136 is obtained from the data store 149. In some embodiments, the motion capture data 136 is obtained from the wearable sensor(s) 106, environmental monitor(s) 109, and/or scanner(s) 119. The motion capture data 136 consists of the movement data 143 and environment data 156 which represent real-time measurements and readings of the patient's movements in the patient's environment during the performance of the balance task 153.

At block 406, the VR-BBS application 159 can calculate a task score 154*a* based at least in part on the motion capture data 136. In some embodiments, the calculation is performed using an algorithm based at least in part on the original BBS zero-to-four scoring metrics.

At block 409, the VR-BBS application 159 can send a task score message 155*b* to the display device 103, where the task score message 155*b* corresponds to the task score 154*a* calculated at block 406. In some embodiments, the VR-BBS application 159 can send the task score message 155*b* to a client device 126.

At block 413, the VR-BBS application 159 can identify a balance task 153 that has yet to be performed by the patient. In some embodiments, the VR-BBS application 159 can search the data store 149 for an unperformed balance task 153. In some embodiments, if the VR-BBS application 159 identifies an unperformed balance task 153, then the VR-BBS application 159 will repeat the steps of blocks 400-413 until the VR-BBS application 159 does not identify an unperformed balance task 153. If the VR-BBS application 159 does not identify an unperformed balance task 153, the VR-BBS application 159 can proceed to block 416.

At block 416, the VR-BBS application 159 can calculate a balance score 154*b*. In some embodiments, the balance score 154*b* is based at least in part upon the one or more task scores 154*a* calculated at block 406. In some embodiments, the balance score 154*b* is based at least in part on the motion capture data 136. In some embodiments, the calculation is performed using an algorithm based at least in part on the original BBS scoring metrics. In some embodiments, the balance score calculation is performed using an algorithm based at least in part on a modified BBS, wherein BBS tasks that would prove hazardous in a virtual reality or augmented reality environment have been removed.

At block 419, the VR-BBS application 159 can send a balance score message 155*c* to the display device 103, where the balance score message 155*c* corresponds to the balance score 154*b* calculated at block 416. In some embodiments, the VR-BBS application 159 can send the balance score message 155*c* to a client device 126.

At block 423, the VR-BBS application 159 can calculate a fall risk score 154*c* based at least in part on the motion capture data 136. In some embodiments, the fall risk score 154*c* is calculated based at least in part on a patient's center-of-mass displacement and/or displacement of the pelvis as determined from the motion capture data 136. In some embodiments, the calculation of the fall risk score 154*c* is performed by an algorithm which considers posturography, jerk, amplitude, and range of acceleration as determined from the motion capture data 136. In some embodiments, the calculation of the fall risk score 154*c* is performed by an algorithm which considers the timing of the task and the maxima of acceleration and velocity during the time for the task.

At block 426, the VR-BBS application 159 can send a fall risk message 155*d* to the display device 103, where the fall risk message 155*d* corresponds to the fall risk score 154*c* calculated at block 423. In some embodiments, the VR-BBS application 159 can send the fall risk message 155*d* to a client device 126.

Figure 5:
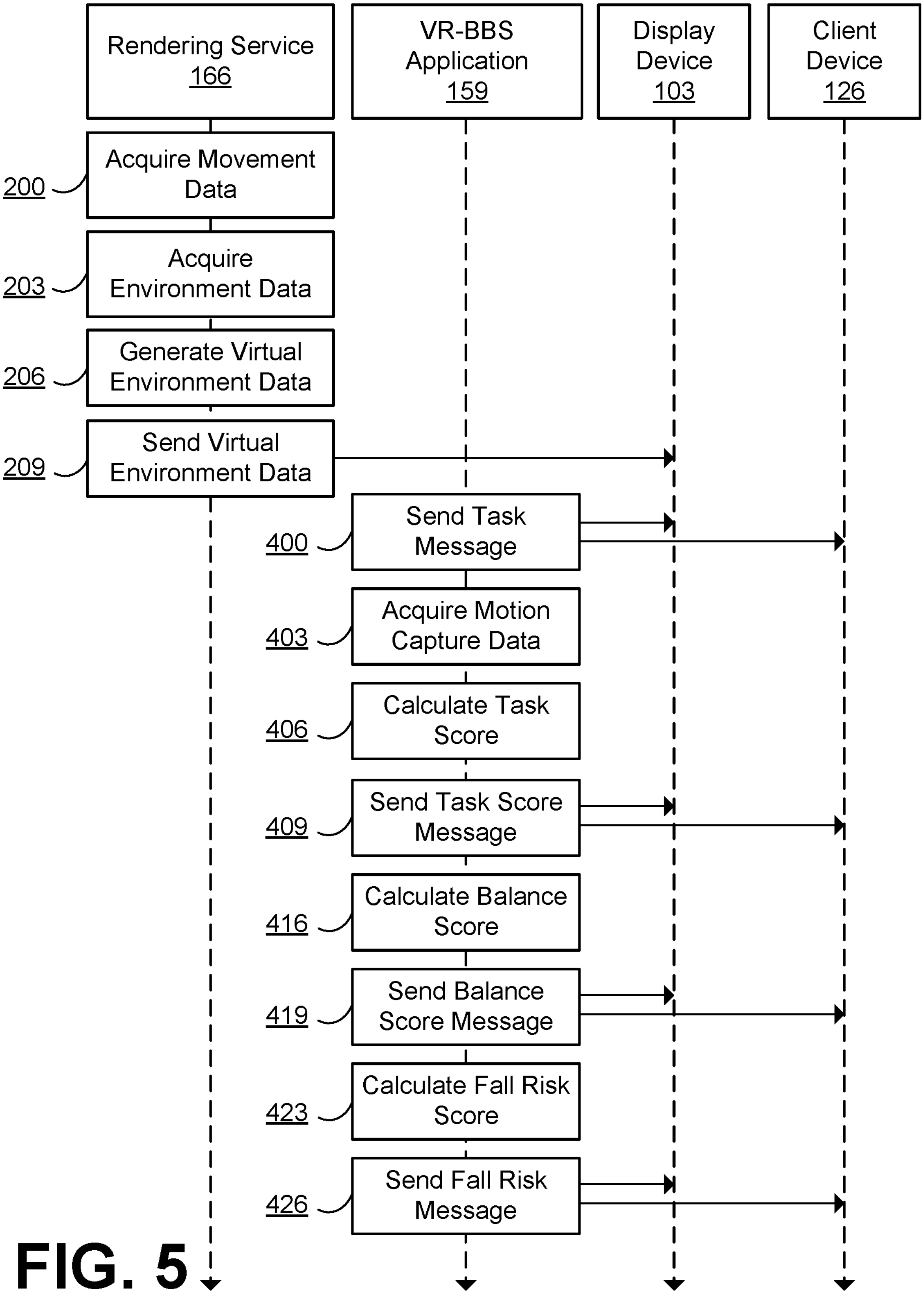
FIG. 5 is a sequence diagram illustrating one example of the interactions between the components of the network environment of FIG. 1 according to various embodiments of the present disclosure.

Referring next to FIG. 5, shown is a sequence diagram that illustrates the interactions between the rendering service 166, the VR-BBS application 159, the display device 103, and the client device 126. The sequence diagram of FIG. 5 provides merely an example of the many different types of functional arrangements that can be employed to implement the operation of the depicted portion between the rendering service 166, the VR-BBS application 159, the display device 103, and the client device 126. As an alternative, the sequence diagram of FIG. 5 can be viewed as depicting an example of elements of a method implemented in the network environment 100.

To begin, the rendering service can acquire the movement data 143 and environment data 156, as previously described in the discussion of blocks 200 and 203 of FIG. 2. The rendering service 166 can generate a virtual environment based at least in part on the movement data 143 and the environment data 156, as previously described in the discussion of block 206 of FIG. 2. The rendering service 166 can send the virtual environment to the display device 103, as previously described in the discussion of block 209 of FIG. 2.

The VR-BBS application 159 can send a task message 155*a* to a display device 103, as previously described in the discussion of block 400 of FIG. 4. The VR-BBS application 159 can acquire motion capture data 136, as previously described in the discussion of block 403 of FIG. 4. The VR-BBS application 159 can calculate a task score 154*a*, as previously described in the discussion of block 406 of FIG. 4. The VR-BBS application 159 can send a task score message 155*b*, as previously described in the discussion of block 409 of FIG. 4. The VR-BBS application 159 can calculate a balance score 154*b*, as previously described in the discussion of block 416 of FIG. 4. The VR-BBS application 159 can send a balance score message 155*c*, as previously described in the discussion of block 419 of FIG. 4. The VR-BBS application 159 can calculate a fall risk score 154*c*, as previously described in the discussion of block 423 of FIG. 4. The VR-BBS application 159 can send a fall risk message 155*d*, as previously described in the discussion of block 426 of FIG. 4. After block 426, the sequence diagram of FIG. 5 ends.

A number of software components previously discussed are stored in the memory of the respective computing devices and are executable by the processor of the respective computing devices. In this respect, the term "executable" means a program file that is in a form that can ultimately be run by the processor. Examples of executable programs can be a compiled program that can be translated into machine code in a format that can be loaded into a random access portion of the memory and run by the processor, source code that can be expressed in a proper format such as object code that is capable of being loaded into a random access portion of the memory and executed by the processor, or source code that can be interpreted by another executable program to generate instructions in a random access portion of the memory to be executed by the processor. An executable program can be stored in any portion or component of the memory, including random access memory (RAM), read-only memory (ROM), hard drive, solid-state drive, Universal Serial Bus (USB) flash drive, memory card, optical disc such as compact disc (CD) or digital versatile disc (DVD), floppy disk, magnetic tape, or other memory components.

The memory includes both volatile and nonvolatile memory and data storage components. Volatile components are those that do not retain data values upon loss of power. Nonvolatile components are those that retain data upon a loss of power. Thus, the memory can include random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, or other memory components, or a combination of any two or more of these memory components. In addition, the RAM can include static random access memory (SRAM), dynamic random access memory (DRAM), or magnetic random access memory (MRAM) and other such devices. The ROM can include a programmable read-only memory (PROM), an erasable programmable read-only memory (EPROM), an electrically erasable programmable read-only memory (EEPROM), or other like memory device.

Although the applications and systems described herein can be embodied in software or code executed by general purpose hardware as discussed above, as an alternative the same can also be embodied in dedicated hardware or a combination of software/general purpose hardware and dedicated hardware. If embodied in dedicated hardware, each can be implemented as a circuit or state machine that employs any one of or a combination of a number of technologies. These technologies can include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts and sequence diagrams show the functionality and operation of an implementation of portions of the various embodiments of the present disclosure. If embodied in software, each block can represent a module, segment, or portion of code that includes program instructions to implement the specified logical function(s). The program instructions can be embodied in the form of source code that includes human-readable statements written in a programming language or machine code that includes numerical instructions recognizable by a suitable execution system such as a processor in a computer system. The machine code can be converted from the source code through various processes. For example, the machine code can be generated from the source code with a compiler prior to execution of the corresponding application. As another example, the machine code can be generated from the source code concurrently with execution with an interpreter. Other approaches can also be used. If embodied in hardware, each block can represent a circuit or a number of interconnected circuits to implement the specified logical function or functions.

Although the flowcharts and sequence diagrams show a specific order of execution, it is understood that the order of execution can differ from that which is depicted. For example, the order of execution of two or more blocks can be scrambled relative to the order shown. Also, two or more blocks shown in succession can be executed concurrently or with partial concurrence. Further, in some embodiments, one or more of the blocks shown in the flowcharts and sequence diagrams can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that includes software or code can be embodied in any non-transitory computer-readable medium for use by or in connection with an instruction execution system such as a processor in a computer system or other system. In this sense, the logic can include statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. Moreover, a collection of distributed computer-readable media located across a plurality of computing devices (e.g., storage area networks or distributed or clustered filesystems or databases) may also be collectively considered as a single non-transitory computer-readable medium.

The computer-readable medium can include any one of many physical media such as magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium can be a random access memory (RAM) including static random access memory (SRAM) and dynamic random access memory (DRAM), or magnetic random access memory (MRAM). In addition, the computer-readable medium can be a read-only memory (ROM), a programmable read-only memory (PROM), an erasable programmable read-only memory (EPROM), an electrically erasable programmable read-only memory (EEPROM), or other type of memory device.

Further, any logic or application described herein can be implemented and structured in a variety of ways. For example, one or more applications described can be implemented as modules or components of a single application. Further, one or more applications described herein can be executed in shared or separate computing devices or a combination thereof. For example, a plurality of the applications described herein can execute in the same computing device, or in multiple computing devices in the same network environment 100.

Disjunctive language such as the phrase "at least one of X, Y, or Z," unless specifically stated otherwise, is otherwise understood with the context as used in general to present that an item, term, etc., can be either X, Y, or Z, or any combination thereof (e.g., X; Y; Z; X or Y; X or Z; Y or Z; X, Y, or Z; etc.). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications can be made to the above-described embodiments without departing substantially from the spirit and principles of the disclosure. All such modifications and variations are intended to be included herein within the scope of this disclosure and protected by the following claims.

Therefore, the following is claimed:

1. A system, comprising:

at least one wearable sensor, wherein at least one of the at least one wearable sensor is configured to be attached to a center of mass of a user;

at least one environmental monitor;

at least one virtual reality headset, wherein the at least one virtual reality headset is configured to be worn on a head of the user;

a computing device comprising a processor and a memory; and machine-readable instructions stored in the memory that, when executed by the processor, cause the computing device to at least:

acquire movement data from the wearable sensor;

acquire environment data from the environmental monitor;

generate a virtual environment based at least in part on the movement data and the environment data;

send the virtual environment to the at least one virtual reality headset;

calculate a balance score based at least in part on a Berg Balance Scale, the movement data, and the environment data; and provide a balance score message based at least in part on the balance score to the at least one virtual reality headset, wherein the balance score message comprises a textual string configured to be displayed on the at least one virtual reality headset.

2. The system of claim 1, wherein the wearable sensor comprises a motion sensor.

3. The system of claim 1, wherein the environmental monitor comprises a camera.

4. The system of claim 1, wherein the machine-readable instructions, when executed by the processor, further cause the computing device to at least:

send a task message to a display device, wherein the task message corresponds to an individual balance task.

5. The system of claim 4, wherein the machine-readable instructions, when executed by the processor, further cause the computing device to at least:

calculate a task score based at least in part on the movement data and the environment data, wherein the task score corresponds to the individual balance task.

6. The system of claim 1, wherein the machine-readable instructions, when executed by the processor, further cause the computing device to at least:

calculate a fall risk score based at least in part on the movement data and the environment data; and send a fall risk message to a display device, wherein the fall risk message corresponds to the fall risk score.

7. A system, comprising:

at least one wearable marker, wherein the at least one wearable marker is configured to be worn by a user;

at least one scanner configured to detect the at least one wearable marker;

at least one virtual reality headset, wherein the at least one virtual reality headset is configured to be worn on a head of the user;

a computing device comprising a processor and a memory; and machine-readable instructions stored in the memory that, when executed by the processor, cause the computing device to at least:

acquire motion capture data from the scanner;

generate a virtual environment based at least in part on the motion capture data;

send the virtual environment to the at least one virtual reality headset;

calculate a balance score of the user based at least in part on a Berg Balance Scale and the motion capture data; and provide a balance score message based at least in part on the balance score to the at least one virtual reality headset, wherein the balance score message comprises a textual string configured to be displayed on the at least one virtual reality headset.

8. The system of claim 7, wherein the wearable marker comprises a light-reflective marker.

9. The system of claim 7, wherein the scanner comprises a LIDAR scanner.

10. The system of claim 7, further comprising:

at least one wearable sensor;

at least one environmental monitor; and wherein the motion capture data is further acquired from at least one of the wearable sensor and the environmental monitor.

11. The system of claim 7, wherein the machine-readable instructions, when executed by the processor, further cause the computing device to at least:

send a task message to a display device, wherein the task message corresponds to an individual balance task.

12. The system of claim 11, wherein the machine-readable instructions, when executed by the processor, further cause the computing device to at least:

calculate a task score based at least in part on the motion capture data, wherein the task score corresponds to the individual balance task.

13. The system of claim 7, wherein the machine-readable instructions, when executed by the processor, further cause the computing device to at least:

calculate a fall risk score based at least in part on the motion capture data; and send a fall risk message to a display device, wherein the fall risk message corresponds to the fall risk score.

14. The system of claim 7, wherein a first display device is the at least one virtual reality headset and the machine-readable instructions, when executed by the processor, further cause the computing device to at least:

send the balance score message to a second display device, wherein the balance score message corresponds to the balance score.

15. The system of claim 1, wherein a first display device is the at least one virtual reality headset and the machine-readable instructions, when executed by the processor, further cause the computing device to at least send the balance score message to a second display device, wherein the balance score message corresponds to the balance score.

16. The system of claim 1, wherein the machine-readable instructions that, when executed by the processor, cause the computing device to generate the virtual environment further cause the computing device to at least generate the virtual environment based at least in part on one or more user inputs.

17. The system of claim 6, wherein the machine-readable instructions that, when executed by the processor, cause the computing device to calculate the fall risk score further cause the computing device to at least calculate the fall risk score based at least in part on a displacement of the center of mass of the user, a displacement of a pelvis of the user, or both.

18. The system of claim 7, wherein the machine-readable instructions that, when executed by the processor, cause the computing device to generate the virtual environment further cause the computing device to at least generate the virtual environment based at least in part on one or more user inputs.

19. The system of claim 7, wherein the scanner comprises an infrared laser emitter.

20. The system of claim 13, wherein the machine-readable instructions that, when executed by the processor, cause the computing device to calculate the fall risk score further cause the computing device to at least calculate the fall risk score based at least in part on a displacement of a center of mass of the user, a displacement of a pelvis of the user, or both.

* * * * *